United States Patent
Hong et al.

(10) Patent No.: US 7,939,694 B2
(45) Date of Patent: May 10, 2011

(54) METHOD FOR THE HYDROFORMYLATION OF OLEFINS AND APPARATUS USING THE SAME

(75) Inventors: Moo-Ho Hong, Daejeon Metropolitan (KR); Dong-Hyun Ko, Daejeon Metropolitan (KR); Sang-Oeb Na, Seoul (KR); Sung-Shik Eom, Daejeon Metropolitan (KR); Sang-Gi Lee, Daejeon Metropolitan (KR); O-Hark Kwon, Daejeon Metropolitan (KR); Dae-Chul Kim, Daejeon Metropolitan (KR); Jae-Hui Choi, Daejeon Metropolitan (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 12/601,858

(22) PCT Filed: May 29, 2008

(86) PCT No.: PCT/KR2008/003029
§ 371 (c)(1),
(2), (4) Date: Nov. 25, 2009

(87) PCT Pub. No.: WO2008/147129
PCT Pub. Date: Dec. 4, 2008

(65) Prior Publication Data
US 2010/0185018 A1    Jul. 22, 2010

(30) Foreign Application Priority Data
May 29, 2007   (KR) .................. 10-2007-0051868

(51) Int. Cl.
*C07C 45/50* (2006.01)
(52) U.S. Cl. .................................... 568/451
(58) Field of Classification Search ............ 568/451
See application file for complete search history.

(56) References Cited

U.S. PATENT DOCUMENTS

| | | | |
|---|---|---|---|
| 4,312,837 A | 1/1982 | Papp et al. | |
| 5,105,018 A | 4/1992 | Miyazawa et al. | |
| 5,410,091 A | 4/1995 | Nall | |
| 5,763,678 A | 6/1998 | Beckers et al. | |
| 6,960,699 B2 | 11/2005 | Totsch et al. | |
| 2001/0003785 A1 | 6/2001 | Protzmann et al. | |
| 2007/0282132 A1 | 12/2007 | Beadle et al. | |

FOREIGN PATENT DOCUMENTS
KR    19980064557 A    10/1998
KR    20020060976       7/2002

OTHER PUBLICATIONS

International Search Report based on PCT/KR2008/003029, dated Oct. 28, 2008, 2 pgs.
Office Action from Korean Application No. 10-2008-0050388, dated Sep. 20, 2009.
Office Action from Korean Application No. 10-2008-0050388, dated Mar. 16, 2010.
Office Action from Korean Application No. 10-2008-0050388, dated May 31, 2010.

*Primary Examiner* — Sikarl A Witherspoon
(74) *Attorney, Agent, or Firm* — Lerner, David, Littenberg, Krumholz & Mentlik, LLP

(57) ABSTRACT

The present invention relates to a method for preparing aldehydes by reacting olefins with a synthesis gas including carbon monoxide and hydrogen, and to an apparatus therefore. More particularly, the present invention relates to a method for preparing aldehydes, characterized by spraying and supplying olefins, synthesis gas including carbon monoxide and hydrogen, and a catalyst composition into an oxo reactor through a nozzle, and to an apparatus therefore. According to the present invention, the hydroformylation efficiency can be improved, thereby obtaining desirable aldehydes with a high yield.

12 Claims, 1 Drawing Sheet

[Figure 1]
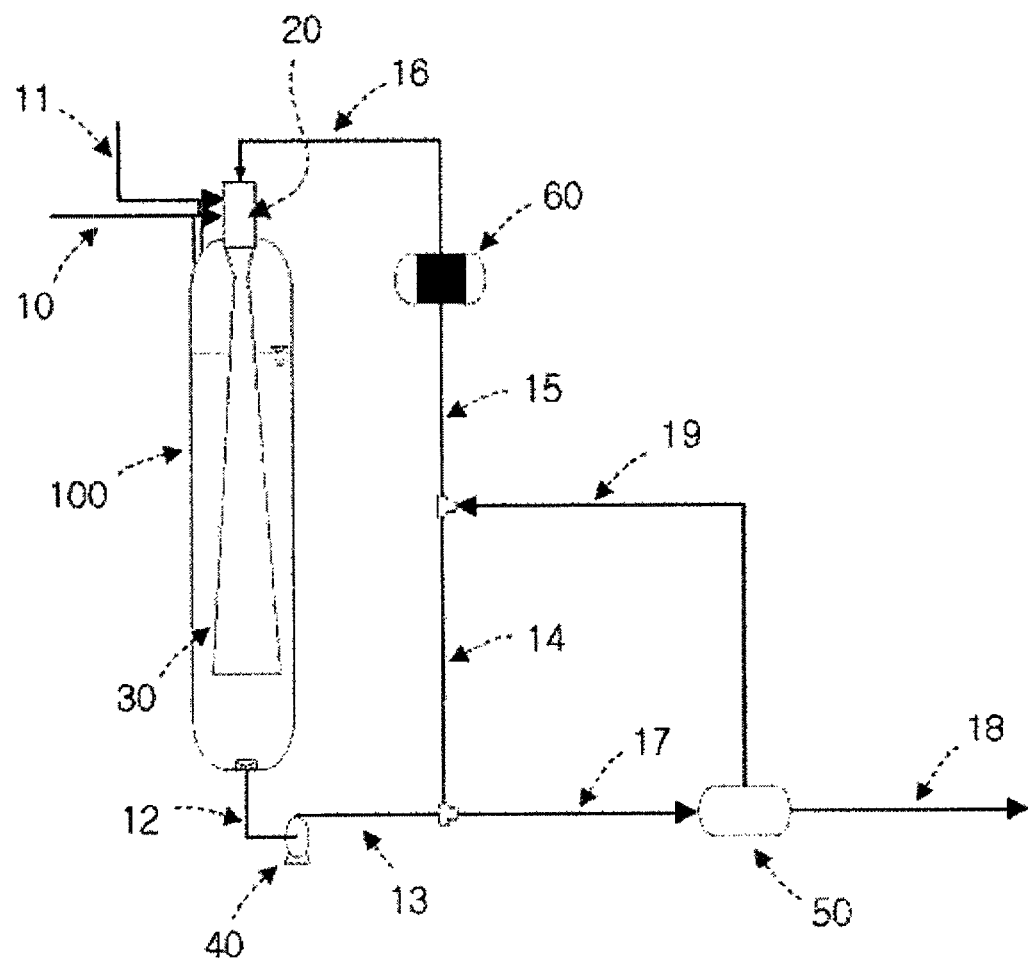

METHOD FOR THE HYDROFORMYLATION OF OLEFINS AND APPARATUS USING THE SAME

TECHNICAL FIELD

The present invention relates to a process for the preparation of aldehydes by hydroformylation of olefins and an apparatus therefore. This application claims priority from Korea Patent Application No. 10-2007-0051868 filed on May 29, 2007 in the KIPO, the disclosure of which is incorporated herein by reference in its entirety.

BACKGROUND ART

The hydroformylation or oxo process is known as a method for the production of saturated aldehydes from olefins, carbon monoxide, and hydrogen in the presence of a catalyst, in which the method involves addition of one hydrogen atom and one formyl group (—CHO) onto a C=C bond. Generally, these aldehydes are subjected to condensation, followed by hydrogenation to give the corresponding alcohols with the longer chain.

The hydroformylation can be exemplified by the preparation of octanol (2-ethylhexanol) from propylene using a rhodium catalyst.

Octanol is mainly used as a raw material for obtaining plasticizers for PVC, such as DOP, and used as an intermediate in the preparation of synthetic lubricants, surfactants or the like. Propylene is injected together with a synthesis gas ($H_2$+CO) into an oxo reactor using a catalyst to generate n-butylaldehyde and iso-butylaldehyde. The produced aldehyde mixture and catalyst mixture are sent to a separation system, and are separated into hydrocarbons and catalyst mixture. Then, the catalyst mixture is recycled to the reactor, and the hydrocarbons are sent to a stripper. The hydrocarbons in the stripper are stripped with the fresh synthesis gas, and the unreacted propylene and synthesis gas are recovered to the oxo reactor. Butylaldehydes are sent to a fractionation column, and separated into n-butylaldehyde and iso-butylaldehyde, respectively. The n-butylaldehyde is introduced from the bottom of the fractionation column into an aldol condensation reactor, followed by condensation and dehydration to give 2-ethylhexenal. The 2-ethylhexenal is sent to a hydrogenation reactor, and thus octanol (2-ethylhexanol) is produced by hydrogenation. The reactants in the outlet of the hydrogenation reactor are sent to a fractionation column, followed by separation of light/heavy ends to give octanol products.

The hydroformylation may be performed in a continuous, semi-continuous, or batch types, and a typical hydroformylation reaction system is a gas or liquid recycle system. On the other hand, in the hydroformylation, it is important to increase reaction efficiency by improvement in contact between liquid and gaseous starting materials, which has been conventionally accomplished by using a continuous stirred tank reactor (CSTR). In addition, in U.S. Pat. No. 5,763,678, disclosed is a hydroformylation process in a series of loop-type reactors which functions as a continuous stirred tank reactor. However, there are limitations in the improvement of the hydroformylation efficiency by the above methods, and it is hard to obtain desirable aldehyde products using a single reactor. Thus, desirable aldehyde products can be generally produced by a longer reaction retention time or two or more reactors connected in series.

DISCLOSURE

Technical Problem

In order to solve the above problems, it is an object of the present invention to provide a method for the preparation of aldehydes from olefins, carbon monoxide, and hydrogen, in which the hydroformylation efficiency is improved to obtain aldehydes with a high yield, and an apparatus used therefore.

Technical Solution

In the present invention, provided is a method for the hydroformylation of olefins, comprising the step of spraying and supplying olefins and a synthesis gas including hydrogen and carbon monoxide through a nozzle into an oxo reactor provided with the nozzle.

In the method for the hydroformylation of olefins, the olefins and synthesis gas may be sprayed and supplied in a molar ratio of 95:5 to 5:95.

In the method for the hydroformylation of olefins, the olefins and synthesis gas may be sprayed and supplied into an oxo reactor through a nozzle in a pressure of 5 to 200 bar, respectively.

In the method for the hydroformylation of olefins, a venturi may be connected to the nozzle.

In the method for the hydroformylation of olefins, the oxo reactor may be a venturi-loop reactor.

In the method for the hydroformylation of olefins, the nozzle may have a diameter of 0.1 mm to 100 cm.

In the method for the hydroformylation of olefins, the flow rate of reaction liquid which is circulated by a pump may be 0.01 to 20 times of charging capacity of the reactor per minute.

In the method for the hydroformylation of olefins, the oxo reactor may be maintained at a temperature of 50 to 200° C. and pressure of 5 to 50 bar.

In the method for the hydroformylation of olefins, the olefin may be propylene, the aldehyde may be butylaldehyde, and the catalyst solution may be a rhodium catalyst solution.

The method for the hydroformylation of olefins may further comprise the step of recovering the reaction mixture from the oxo reactor.

The method for the hydroformylation of olefins may further comprise the step of separating aldehydes from the reaction mixture.

The method for the hydroformylation of olefins may further comprise the step of supplying the catalyst mixture, which is resulting from the separation of aldehydes from the reaction mixture, through a nozzle provided in the oxo reactor.

In addition, the present invention provides an apparatus for the hydroformylation of olefins, comprising an oxo reactor provided with a nozzle; an olefin feed line and a synthesis gas feed line for feeding a synthesis gas including hydrogen and carbon monoxide which are connected to the nozzle, respectively; a recycling line for recovering the reaction mixture which is recovered from the oxo reactor to supply into the nozzle provided in the oxo reactor; a separation line branching off from any position in the recycling line; a catalyst/aldehyde separator connected to the separation line; a catalyst solution feed line connected to any position in the catalyst/aldehyde separator and recycling line; and an aldehyde recovery line which is connected to the catalyst/aldehyde separator.

In the apparatus for the hydroformylation of olefins, the nozzle may be provided at the top portion inside the oxo reactor.

In the apparatus for the hydroformylation of olefins, a venturi may be connected to the nozzle.

In the apparatus for the hydroformylation of olefins, the oxo reactor may be a venturi-loop reactor.

In the apparatus for the hydroformylation of olefins, the nozzle may have a diameter of 0.1 mm to 100 cm.

In the method for the hydroformylation of olefins, the flow rate of reaction liquid which is circulated by a pump may be 0.01 to 20 times of charging capacity of the reactor per minute.

In the apparatus for the hydroformylation of olefins, a circulating pump may be provided at any position of the recycling line which connects the bottom portion of the oxo reactor with the nozzle.

In the apparatus for the hydroformylation of olefins, a heat exchanger may be provided at any position of the recycling line which connects the bottom portion of the oxo reactor with the nozzle.

ADVANTAGEOUS EFFECTS

The present invention provides a method for the preparation of aldehydes by hydroformylation of olefins, in which the hydroformylation efficiency is improved, thereby obtaining desirable aldehydes with a high yield.

DESCRIPTION OF DRAWINGS

FIG. 1 is a schematic diagram showing the process for the hydroformylation of olefins according to one embodiment of the present invention.

DESCRIPTION OF MARKS OF THE DRAWINGS

| 10: | Olefin feed line | 11: | Synthesis gas feed line |
|---|---|---|---|
| 12, 13, 14, 15, 16: | Recycling line | | |
| 17: | Separation line | 18: | Aldehyde recovery line |
| 19: | Catalyst solution feed line | 20: | Nozzle |
| 30: | Venturi | 40: | Circulating pump |
| 50: | Catalyst/aldehyde separation apparatus | | |
| 60: | Heat exchanger | 100: | Oxo reactor |

BEST MODE

Hereinafter, the present invention will be described in detail.

Preferred examples of the olefins used in the present invention include ethylene, propylene, butene, 1-hexene, 1-octene, 1-nonene, 1-decene, 1-undecene, 1-tridecene, 1-tetradecene, 1-pentadecene, 1-hexadecene, 1-heptadecene, 1-octadecene, 1-nonadecene, 1-eicosene, 2-butene, 2-methyl propene, 2-pentene, 2-hexene, 2-heptene, 2-ethyl hexene, 2-octene, styrene, 3-phenyl-1-propene, 1,4-hexadiene, 1,7-octadiene, 3-cyclohexyl-1-butene, allyl acetate, allyl butyrate, methyl methacrylate, vinyl methyl ether, vinyl ethyl ether, allyl ethyl ether, n-propyl-7-octenoate, 3-butenenitrile, 5-hexenamide, 4-methyl styrene, 4-isopropyl styrene.

The typical process according to the present invention includes the hydroformylation of propylene into n- and iso-butylaldehydes using a rhodium catalyst.

The prepared aldehydes according to the present invention may be subjected to hydrogenation, and thus converted into corresponding alcohols which may be used as a solvent and for the preparation of plasticizer.

In the hydroformylation of olefins, homogeneous catalysts using a group VIII transition metal including rhodium (Rh), cobalt (Co), and iridium (Ir) as a main ingredient may be used, and hydride (H$^-$), carbonyl (CO), tripenylphosphine (TPP) may be used as a ligand, but are not limited thereto, any one known in the art may be used. The rhodium catalyst is highly expensive, but provides more stable reaction conditions, excellent catalytic activity and high selectivity during the hydroformylation process, compared to the cobalt or iridium catalyst. Thus, the rhodium catalyst is generally employed in the commercialized process.

Olefins, as a starting material, are sprayed and supplied together with a synthesis gas (syn gas) including carbon monoxide and hydrogen through the nozzle which is provided in the oxo reactor. The nozzle is preferably provided at the top portion inside the oxo reactor. The nozzle which is provided in the oxo reactor may have various diameters depending on the size of the reactor, 0.1 mm to 100 cm, and preferably 1 mm to 50 cm. The nozzle may consist of multiple nozzles of two or more.

The olefins and synthesis gas are sprayed and supplied into the oxo reactor through the nozzle at a feeding pressure of 1 to 200 bar, respectively. The molar ratio of olefin: synthesis gas supplied into the oxo reactor is about 95:5 to 5:95, and more preferably 75:25 to 25:75. The hydroformylation reaction is performed at a temperature of 50 to 200° C. and a pressure of 5 to 100 bar, and more preferably at a temperature of 50 to 150° C. and a pressure of 5 to 50 bar.

Unlike the conventional hydroformylation process using a continuous stirred tank reactor (CSTR), a continuous reactor equipped with the nozzle or both nozzle and venturi of the present invention facilitates gas-liquid contact during the hydroformylation reaction, thereby greatly increasing the reaction efficiency.

In particular, in the case of using a continuous reactor equipped with nozzle and venturi (venturi-loop reactor), the starting materials, olefins and synthesis gas ($CO+H_2$) are spayed into the venturi through the nozzle to more facilitate gas-liquid contact, thereby maximizing the reaction efficiency.

In the case of using a circular type reactor for the hydroformylation reaction, some of the products (reaction mixture) may be reused as a reactant (starting material). The reaction mixture recovered from the bottom portion of the oxo reactor contains aldehydes, unconverted olefins and catalyst solution. The desired aldehydes may be separated from the reaction mixture using a separator. The separated aldehydes are recovered, and the catalyst mixture, resulting from the separation of aldehydes from the reaction mixture, is sprayed and supplied into the oxo reactor through the nozzle provided in the oxo reactor.

The preferred process using the method of the present invention may be understood more readily by reference to the accompanying drawings. In FIG. 1, omitted are practical standard installations such as a valve, a temperature sensor, and a pressure sensor, which are easily recognized by those skilled in the art.

FIG. 1 is a schematic diagram showing the process for the hydroformylation of olefins according to one embodiment of the present invention. Olefins (e.g., propylene) and synthesis gas (carbon monoxide+hydrogen) are supplied into the nozzle 20, which is provided at the top portion of the oxo reactor 100 charged with the catalyst solution, through the olefin feed line 10 and the synthesis gas feed line 11, respectively.

In order to improve the efficiency of the gas-liquid reaction, the nozzle 20 and the venturi 30 which is connected to the nozzle are installed inside the oxo reactor 100, and the supplied olefins and synthesis gas are continuously sprayed and supplied into the venturi 30 through the nozzle 20. As such, the oxo reactor 100 may be a reactor equipped with the nozzle or both nozzle and venturi for the purpose of improving the efficiency of the gas-liquid reaction, preferably venturi-loop reactor. The olefins and synthesis gas, which had been sprayed into the oxo reactor, undergo hydroformylation in the presence of a catalyst to generate the reaction mixture. The reaction mixture contains unconverted olefins, by-products, and the catalyst solution, in addition to the desired aldehydes (e.g., n- and iso-butylaldehydes).

The reaction mixture containing the aldehydes is recovered through a recycling line 12 using a circulating pump 40, and then circulated through the recycling line 13 into the nozzle 20 provided in the reactor, in which some of the circulated reaction mixture may be sent to a catalyst/aldehyde separator 50 through a separation line 17 branching off from the recycling line 13 in order to separate aldehydes.

As the catalyst/aldehyde separator 50 for the separation of aldehydes, any means capable of separating the aldehydes from the reaction mixture maybe used without limitations. The recovered aldehydes maybe sent to the separation/recovery device and the like (not shown) through the aldehyde recovery line 18, and various aldehydes and condensation products may be separated, recovered by the conventional distillation apparatus and the like. For example, during the hydroformylation process of producing butylaldehydes from propylenes, the recovered butylaldehydes recovered from the oxo reactor are sent to the fractionation column, and separated into n- and iso-butylaldehydes, respectively. The n-butylaldehydes in the bottom of the fractionation column are introduced into an aldol condensation reactor, followed by hydrogenation to give octanol (2-ethyl hexanol).

The residual catalyst mixture, resulting from separation of the desired aldehydes from the reaction mixture, is supplied into the recycling line 15 of the oxo reactor 100 through a catalyst solution recycling line 19.

The reaction mixture of the reactor which is combined with the recycled catalyst mixture is passed through a heat exchanger 60, and sprayed and supplied through the nozzle provided in the oxo reactor 100 into the oxo reactor 100 together with the olefins and synthesis gas which are supplied through the olefin feed line 10 and synthesis gas feed line 11.

The recirculation of the catalyst mixture, from which the desired materials are removed, maybe continuously performed. If necessary, some of the recirculating reaction mixture may be discharged to regenerate the catalyst or a fresh catalyst solution or reactivated catalyst solution may be added to the recirculating stream of the reaction mixture. FIG. 1 shows an example of introducing the residual catalyst solution or the reactivated catalyst solution into the reactor system by connecting the catalyst solution recycling line 19 between the recycling lines 14 and 15.

The heat exchanger 60 may be provided between the recycling lines (15 and 16), but the position is not particularly limited. The heat exchanger 60 functions to maintain the temperature of the reaction mixture, which is recirculated into the oxo reactor 100, within a range suitable for hydroformylation reaction.

MODE FOR INVENITON

Hereinafter, the present invention will be described in more detail with reference to preferred Examples. However, these Examples are for illustrative purposes only, and the invention is not intended to be limited by these Examples.

EXAMPLE 1

As shown in FIG. 1, a venturi-loop reactor having a capacity of 3 liters was manufactured and installed. Instead of an external heat exchanger, the internal temperature of the reactor was maintained by flowing heat transfer oil in a jacket. The venturi-loop reactor was equipped with a nozzle having a diameter of 1.7 mm, and the expansion tube had a diameter of 8.0 mm and a length of 200 mm. 48 g of triphenylphosphine (TPP) and 0.8 g (by weight) of rhodium (triphenylphosphine) acetylacetonatecarbonyl (ROPAC) were dissolved in 800 g of refined n-butylaldehyde to prepare a n-butylaldehyde catalyst solution. The prepared catalyst solution was injected into the reactor, and the circulating pump was operated to slowly circulate the catalyst solution at a rate of 2 liter per minute. The entire system was purged with the refined nitrogen gas through the nozzle at the top portion of the reactor three times. While maintaining the external circulating pump at a rate of 2 liter per minute, the internal temperature of the reactor was increased and maintained at 90° C. by flowing heat transfer oil in an external jacket of the venturi-loop reactor. When the temperature was stably maintained at 90° C., propylene was supplied at a speed of 12 g/min until the reactor was pressurized to 16.2 barg. After confirming that the internal temperature of the venturi-loop reactor was maintained at 90° C. for 5 min, the synthesis gas (mixed gas of carbon monoxide and hydrogen at a molar ratio of 50:50) was supplied into a neck of the nozzle (10 in FIG. 1) at a pre-set feeding pressure of 18.8 barg and the reaction was simultaneously initiated. While the internal temperature of the venturi-loop reactor was maintained at 90° C. by using an automatic temperature control device connected to the reactor, the flow rate of the synthesis gas supplied into the reactor was measured. After 2 hrs, the mixed gas was cut off, and then the operation of circulating pump was immediately stopped. The reactor temperature was reduced to room temperature, and then the pressure was released. The mixture of total catalyst solution and products was recovered through a separation line, and its weight was measured. As a result, the weight of total solution (after reaction) was found to be 1,265 g, and thus the weight of the resulting butylaldehyde was found to be 465 g. In addition, the total amount of consumed synthesis gas was measured using an integrated flow meter installed in the synthesis gas feed line. During reaction, the maximum consumption rate of the synthesis gas was found to be 5.4 liter per minute.

EXAMPLE 2

The experiment was performed in the same manners as in Example 1, except that the circulating rate of the circulating pump was reduced to 1.0 liter per minute. After 2 hrs, the total weight of the obtained catalyst solution and products was found to be 1,225 g, and thus the weight of the resulting butylaldehyde was found to be 420 g. During reaction, the maximum consumption rate of the synthesis gas was found to be 4.1 liter per minute.

EXAMPLE 3

The experiment was performed in the same manners as in Example 1, except that the diameter of the nozzle installed in the venturi-loop reactor was changed to 4 mm. After 2 hrs, the total weight of the obtained catalyst solution and products was found to be 1,240 g, and thus the weight of the resulting butylaldehyde was found to be 440 g. During reaction, the maximum consumption rate of the synthesis gas was found to be 4.6 liter per minute.

COMPARATIVE EXAMPLE 1

The experiment was performed in the same manners as in Example 1, except for supplying the synthesis gas into the circulating line (16 in FIG. 1) at the top portion of the nozzle instead of the neck of the nozzle (10 in FIG. 1) in the venturi-loop reactor as in Example 1. The weight of the resulting butylaldehyde was found to be 412 g. During reaction, the maximum consumption rate of the synthesis gas was found to be 4.0 liter per minute.

COMPARATIVE EXAMPLE 2

While supplying the synthesis gas in the same manners as in Example 1 and maintaining the stirrer at a speed of 1000 rpm, the experiment was performed for 2 hrs, except for using an autoclave reactor having a capacity of 3 liters instead of the venturi-loop reactor of Example 1. The weight of the resulting butylaldehyde was found to be 403 g. During reaction, the maximum consumption rate of the synthesis gas was found to be 3.9 liter per minute.

INDUSTRIAL APPLICABILITY

The present invention provides a method for the preparation of aldehydes by hydroformylation of olefins, in which the hydroformylation efficiency is improved, thereby obtaining desirable aldehydes with a high yield.

The invention claimed is:

1. A method for the hydroformylation of olefins, comprising the step of spraying and supplying olefins and a synthesis gas including hydrogen and carbon monoxide through a nozzle into an oxo reactor which is provided with the nozzle connected with a venturi and a recycling line.

2. The method for the hydroformylation of olefins according to claim 1, wherein the olefins and synthesis gas are sprayed and supplied in a molar ratio of 95:5 to 5:95.

3. The method for the hydroformylation of olefins according to claim 1, wherein the olefins and synthesis gas are sprayed and supplied into the oxo reactor through the nozzle at a feeding pressure of 1 to 200 bar, respectively.

4. The method for the hydroformylation of olefins according to claim 1, wherein the oxo reactor is a venturi-loop reactor.

5. The method for the hydroformylation of olefins according to claim 1, wherein the nozzle has a diameter of 0.1 mm to 100 cm.

6. The method for the hydroformylation of olefins according to claim 1, wherein the flow rate of the fluid circulating through the recycling line is 0.01 to 20 times of charging capacity of the reactor per minute.

7. The method for the hydroformylation of olefins according to claim 1, wherein the oxo reactor is maintained at a temperature of 50 to 200° C. and a pressure of 5 to 50 bar.

8. The method for the hydroformylation of olefins according to claim 1, wherein the olefin is propylene.

9. The method for the hydroformylation of olefins according to claim 8, further comprising adding a rhodium catalyst to the oxo reactor.

10. The method for the hydroformylation of olefins according to claim 1, further comprising a step of recovering a reaction mixture from the oxo reactor.

11. The method for the hydroformylation of olefins according to claim 10, further comprising a step of separating aldehydes from the reaction mixture.

12. The method for the hydroformylation of olefins according to claim 11, further comprising a step of supplying a catalyst mixture, which is resulting from the separation of aldehydes from the reaction mixture, through the nozzle provided in the oxo reactor.

\* \* \* \* \*